United States Patent [19]
Kleiner et al.

[11] Patent Number: 5,811,567
[45] Date of Patent: Sep. 22, 1998

[54] PROCESS FOR PREPARING THE CRYSTAL MODIFICATION OF 2,2',2"-NITRILO[TRIETHYL TRIS(3,3',5,5'-TETRA-TERT-BUTYL-1,1'-BIPHENYL-2,2'-DIYL) PHOSPHITE]

[76] Inventors: Hans-Jerg Kleiner; Gerhard Pfahler, both of Hoechst Aktiengesellschaft, D-65926 Frankfurt am Main, Germany

[21] Appl. No.: 877,001

[22] Filed: Jun. 16, 1997

[30] Foreign Application Priority Data

Jun. 19, 1996 [DE] Germany .................. 196 24 424.2

[51] Int. Cl.$^6$ .................................. C07F 9/6574
[52] U.S. Cl. ................ 558/78; 252/49.9; 252/400.21; 524/111; 524/119
[58] Field of Search ................................ 558/78

[56] References Cited

U.S. PATENT DOCUMENTS

| | | | |
|---|---|---|---|
| 4,374,219 | 2/1983 | Spivack et al. | 524/91 |
| 5,276,076 | 1/1994 | Pastor et al. | 558/78 X |
| 5,373,040 | 12/1994 | Pastor et al. | 524/119 |
| 5,405,893 | 4/1995 | Pastor et al. | 524/119 |
| 5,486,641 | 1/1996 | Shum et al. | 558/78 |
| 5,512,621 | 4/1996 | Pastor et al. | 558/78 X |

FOREIGN PATENT DOCUMENTS

| | | |
|---|---|---|
| 94/12506 | 6/1994 | WIPO . |
| 94/12508 | 6/1994 | WIPO . |
| 94/12509 | 6/1994 | WIPO . |
| 95/05387 | 2/1995 | WIPO . |

*Primary Examiner*—Michael G. Ambrose
*Attorney, Agent, or Firm*—Connolly & Hutz

[57] ABSTRACT

The present invention relates to a process for preparing the α crystal modification of 2,2',2"—nitrilo[triethyltris(3,3',5,5"—tetra—tert—butyl—1,1'—biphenyl—2,2'—diyl) phosphite] (abbreviated as NTTBP) of the formula

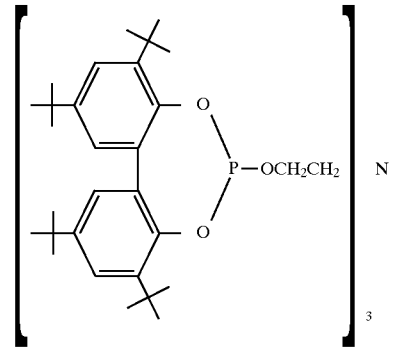

which comprises dissolving the NTTBP in the form of its melt, its amorphous solid-phase modification or its β crystal modification, hot, at 40 to 100° C., in short-chain ketones having 3 to 7 carbon atoms, such as methyl ethyl ketone or, in particular, acetone, and then initiating crystallization by cooling to room temperature.

3 Claims, No Drawings

PROCESS FOR PREPARING THE CRYSTAL MODIFICATION OF 2,2',2"-NITRILO[TRIETHYL TRIS(3,3',5,5'-TETRA-TERT-BUTYL-1,1'-BIPHENYL-2,2'-DIYL) PHOSPHITE]

DESCRIPTION

Process for preparing the α crystal modification of 2,2', 2"—nitrilo[triethyl tris(3,3',5,5'—tetra—tert—butyl—1, 1'—biphenyl—2,2'—diyl) phosphite]

2,2',2"—Nitrilo[triethyl tris(3,3',5,5'—tetra—tert—butyl—1,1'—biphenyl—2,2'—diyl) phosphite] (abbreviated as NTTBP) is a valuable stabilizer for polymers (see U.S. Pat. No. 4,318,845 and U.S. Pat. No. 4,374,219) and, in addition to amorphous solid-phase modification (U.S. Pat. No. 5,276,076 and U.S. Pat. No. 5,373,040), occurs in three different crystalline modifications (α modification: WO 94/12509, β modification: WO 94/12508 and γ modification: WO 95/03587).

NTTBP is prepared to date in accordance with U.S. Pat. No. 4,318,845 (Example 4) in such a manner that, in a first process step, starting from phosphorus trichloride and 2,2', 4,4'—tetra—tert—butyl—o—o'—bisphenol, 6—chloro—2,4,8,10—tetra—tert—butylbenzo—[d,f][1,3,2] dioxaphosphepine (abbreviated as chloro—phosphite) is prepared in solution and a mixture of triethanolamine and triethylamine is added dropwise to the solution. After reaction is completed, the mixture is filtered off from triethylamine hydrochloride with suction and the solvent is removed by distillation. The NTTBP remains as crude product in the amorphous solid-phase modification. After recrystallizing twice from acetonitrile/toluene, NTTBP is obtained as a white powder having a melting point of 121° –134° C. in a yield of only slightly over 70%, which is not very satisfactory.

Our own studies have found that NTTBP prepared by this method is essentially present in the α modification. In order to obtain the α modification in completely pure form, it is necessary in accordance with WO 94/12509 to recrystallize again the material having a melting point of 121° –134° C. using certain solvents or solvent mixtures, such as ethyl acetate, toluene/isopropanol or diethyl ether.

On the whole, the α crystal modification of NTTBP is only present in a purity completely satisfactory for use after recrystallization for the third time.

There was therefore a requirement for a process which makes the α crystal modification of NTTBP accessible in a technically simple manner and with a more satisfactory yield.

The object is achieved by a process for preparing the α crystal modification of NTTBP of the formula

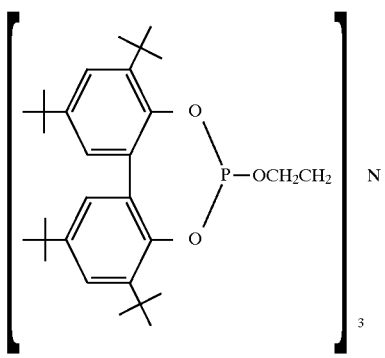

which comprises dissolving the NTTBP in the form of its melt, its amorphous solid-phase modification or its β crystal modification in short-chain ketones having 3 to 7 carbon atoms, hot, at 40° to 100° C., in particular 50° to 70° C., and then initiating crystallization by cooling to room temperature.

Short-chain ketones which may be mentioned, are, in particular, methyl ethyl ketone and acetone. Particular preference is given to acetone.

The process according to the invention permits the use of the crude product which is produced in the preparation process according to U.S. Pat. No. 4,318,845 or U.S. Pat. No. 4,374,219. Particular preference is given to the crude product as is produced in accordance with the process of Example 1 (introduction of the mixture of triethanolamine and triethylamine, addition of the chlorophosphite solution).

In addition, the process according to the invention permits the conversion of the β crystal modification into the α crystal modification. The preparation of the β modification is described in WO 94/12508 mentioned at the outset.

EXAMPLE 1

24.32 g (0.163 mol) of triethanolamine and 49.48 g (0.489 mol) of triethylamine are dissolved in 200 ml of o—xylene and 50 ml of tetrahydrofuran. A hot (60° C.) solution of 232 g (0.489 mol) of chlorophosphite in 800 ml of o—xylene is added dropwise to this mixture at −5° to 0° C. with stirring over 75 minutes. After addition is completed, the mixture is heated to room temperature and subsequently stirred for about 60 hours. The amine hydrochloride is then filtered off with suction and rinsed with o—xylene. The filtrate is distilled at atmospheric pressure to an internal temperature of 160°–176° C. The resulting melt is then rapidly poured into 500 ml of acetone. A clear solution is obtained, the NTTBP crystallizes out on cooling, is separated off and rinsed with acetone, then dried under reduced pressure at 50° C. 224.4 g having a melting point of 154°–158° C. are obtained (degree of purity according to 31-P-NMR: 99.4% pure) of the α modification. This corresponds to a yield of 94% of theory.

EXAMPLE 2

10 g of α crystal modification (melting point: 205° C.) are dissolved in 300 ml of acetone under reflux conditions. The solution is then cooled to room temperature. After recrystallization is completed, the product is filtered off with suction. 7.5 g of α crystal modification having a melting point of 162°–164° C. are obtained. This corresponds to a yield of 75% of theory.

EXAMPLE 3

50 g of β crystal modification (melting point: 205° C.) are dissolved in 150 ml of acetone or methyl ethyl ketone at approximately 70° C. The solution is then cooled to room temperature. After standing for a relatively long period, the α crystal modification crystallizes out. The product is filtered off with suction and dried under reduced pressure at 80° C. 35 g having a melting point of 148°–153° C. are obtained. This corresponds to a yield of 70% of theory.

We claim:

1. A process for preparing the α crystal modification of 2,2',2"—nitrilo[triethyltris(3,3',5,5"—tetra—tert—butyl—1,1'—biphenyl—2,2'—diyl) phosphite] (abbreviated as NTTBP) of the formula

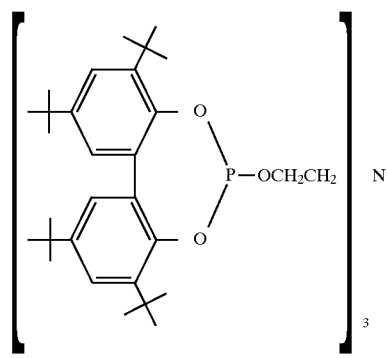

which comprises dissolving the NTTBP in the form of its melt, its amorphous solid-phase modification or its β crystal modification in short-chain ketones having 3 to 7 carbon atoms, hot, at 40° to 100° C., and then initiating crystallization by cooling to room temperature.

2. A process as claimed in claim 1, wherein the short-chain ketone used is methyl ethyl ketone.

3. A process as claimed in claim 1, wherein the short-chain ketone used is acetone.

* * * * *